US00PP36161P2

(12) United States Plant Patent
Bisschop et al.

(10) Patent No.: US PP36,161 P2
(45) Date of Patent: Sep. 24, 2024

(54) ***HELLEBORUS* PLANT NAMED 'ET EPB 855'**

(50) Latin Name: ***Helleborus orientalis* X *Helleborus ericsmithii***
Varietal Denomination: ET EPB 855

(71) Applicant: ETERNAL PLANT BOIJL B.V., Boijl (NL)

(72) Inventors: Elisabeth Bisschop, Boijl (NL); Bart Noordhuis, Boijl (NL)

(73) Assignee: ETERNAL PLANTS BOIJL B.V., Boijl (NL)

( * ) Notice: Subject to any disclaimer, the term of this patent is extended or adjusted under 35 U.S.C. 154(b) by 0 days.

(21) Appl. No.: 18/421,802

(22) Filed: Jan. 24, 2024

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'ET EPB 855', characterized by its relatively compact and upright plant habit; moderately vigorous to vigorous growth habit; dark green-colored leaves with lighter green-colored marbling; continuous and freely flowering habit; relatively large yellowish green-colored flowers with deep purplish red-colored margins and venation that are held above the foliar plane on relatively long peduncles; and good garden performance.

2 Drawing Sheets

Figure 1:
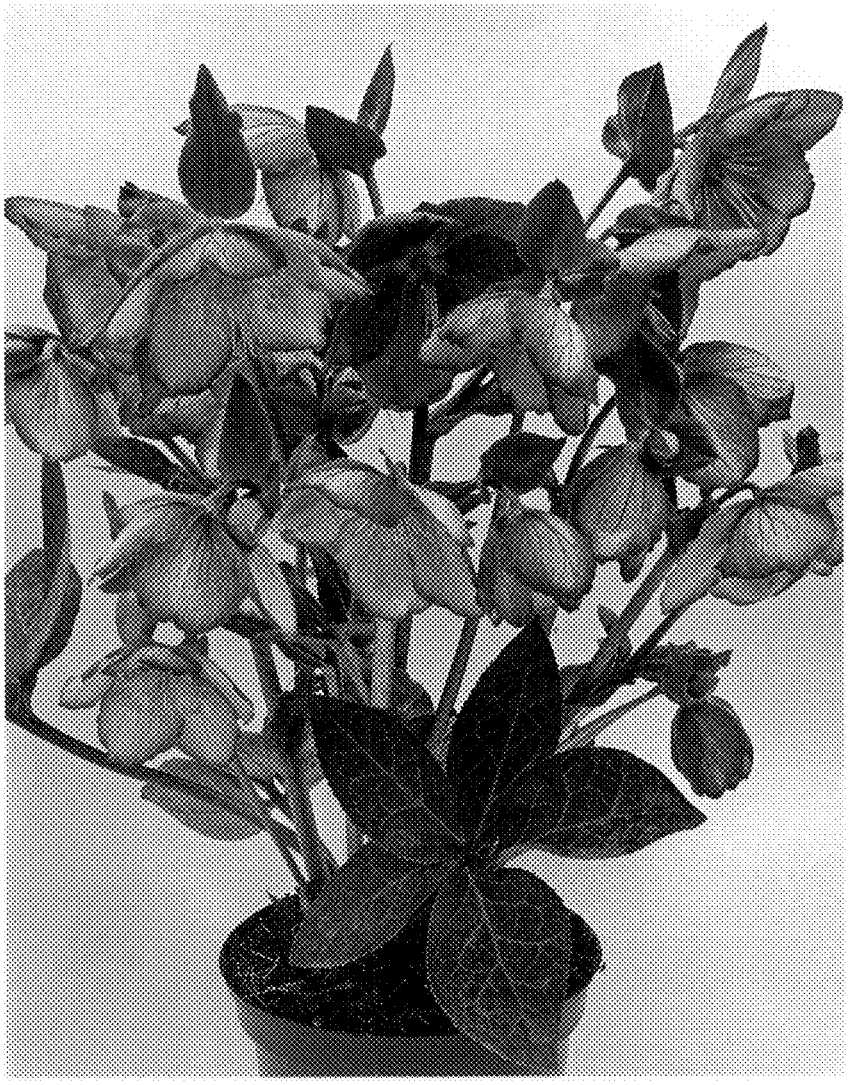

Botanical designation: *Helleborus orientalis* X *Helleborus ericsmithii.*

Cultivar denomination: 'ET EPB 855'.

STATEMENT REGARDING PRIOR DISCLOSURES BY INVENTORS & APPLICANT/ASSIGNEE

The Inventors and Applicant/Assignee assert that no sales, offers for sale or public distribution of the instant plant occurred more than one year prior to the effective filing date of this application.

Any information about the claimed plant would have been obtained from a direct or indirect disclosure from the Inventors and/or Applicant/Assignee. Inventors and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Helleborus* plant, botanically known as *Helleborus orientalis X Helleborus ericsmithii* and hereinafter referred to by the name 'ET EPB 855'.

The new *Helleborus* plant is a product of a planned breeding program conducted by the Inventors in Boijl, The Netherlands. The objective of the breeding program was to create new freely-flowering *Helleborus* plants with strong peduncles that hold attractive flowers above the foliar plane.

The new *Helleborus* plant originated from a cross-pollination conducted by the Inventors in Boijl, The Netherlands on Feb. 8, 2017 of a proprietary selection of *Helleborus orientalis* identified as code number O15-315, not patented, as the female, or seed, parent with a proprietary selection of

*Helleborus ericsmithii* identified as code number P14-1603, not patented, as the male, or pollen, parent. The new *Helleborus* plant was discovered and selected by the Inventors as a single flowering plant from within the progeny of the stated cross-pollination grown in a controlled greenhouse environment in Boijl, The Netherlands on Feb. 1, 2018.

Asexual reproduction of the new *Helleborus* plant by meristem culture in a controlled greenhouse environment in Boijl, The Netherlands since May 3, 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'ET EPB 855'. These characteristics in combination distinguish 'ET EPB 855' as a new and distinct *Helleborus* plant:

1. Relatively compact and upright plant habit.
2. Moderately vigorous to vigorous growth habit.
3. Dark green-colored leaves with lighter green-colored marbling.
4. Continuous and freely flowering habit.
5. Relatively large yellowish green-colored flowers with deep purplish red-colored margins and venation that are held above the foliar plane on relatively long peduncles.
6. Good garden performance.

Plants of the new *Helleborus* differ from plants of the female parent selection in the following characteristics:

1. Plants of the new *Helleborus* are more compact than and not as vigorous as plants of the female parent selection.
2. Leaves of plants of the new *Helleborus* are stronger and stiffer than and not as floppy as leaves of plants of the female parent selection.
3. Plants of the new *Helleborus* are more freely flowering than plants of the female parent selection.

Plants of the new *Helleborus* differ from plants of the male parent selection in the following characteristics:

1. Plants of the new *Helleborus* are more compact than and not as vigorous as plants of the male parent selection.
2. Leaves of plants of the new *Helleborus* are stronger and stiffer than and not as floppy as leaves of plants of the male parent selection.
3. Plants of the new *Helleborus* are more freely flowering than plants of the male parent selection.

Plants of the new *Helleborus* can be compared to plants of *Helleborus x hybridus* 'EPB 29', disclosed in U.S. Plant Pat. No. 28,010. In side-by-side comparisons, plants of the new *Helleborus* differ from plants of 'EPB 29' in the following characteristics:

1. Plants of the new *Helleborus* are taller and broader than plants of 'EPB 29'.
2. Plants of the new *Helleborus* have smaller leaves than plants of 'EPB 29'.
3. Plants of the new *Helleborus* are more freely flowering and flower for a longer period of time than plants of 'EPB 29'.
4. Plants of the new *Helleborus* have larger flowers than plants of 'EPB 29'.
5. Plants of the new Helleborus have longer peduncles than plants of 'EPB 29'.

Plants of the new *Helleborus* can also be compared to plants of *Helleborus x hybridus* 'EPB 25', disclosed in U.S. Plant Pat. No. 28,080. In side-by-side comparisons, plants of the new *Helleborus* differ from plants of 'EPB 25' in the following characteristics:

1. Plants of the new *Helleborus* are more compact than plants of 'EPB 25'.
2. Plants of the new *Helleborus* have larger flowers than plants of 'EPB 25'.
3. Flowers of plants of the new *Helleborus* are more star-shaped than and not as rounded as flowers of plants of 'EPB 25'.

BRIEF DESCRIPTION OF THE PHOTOGRAPHS

Figure 2:
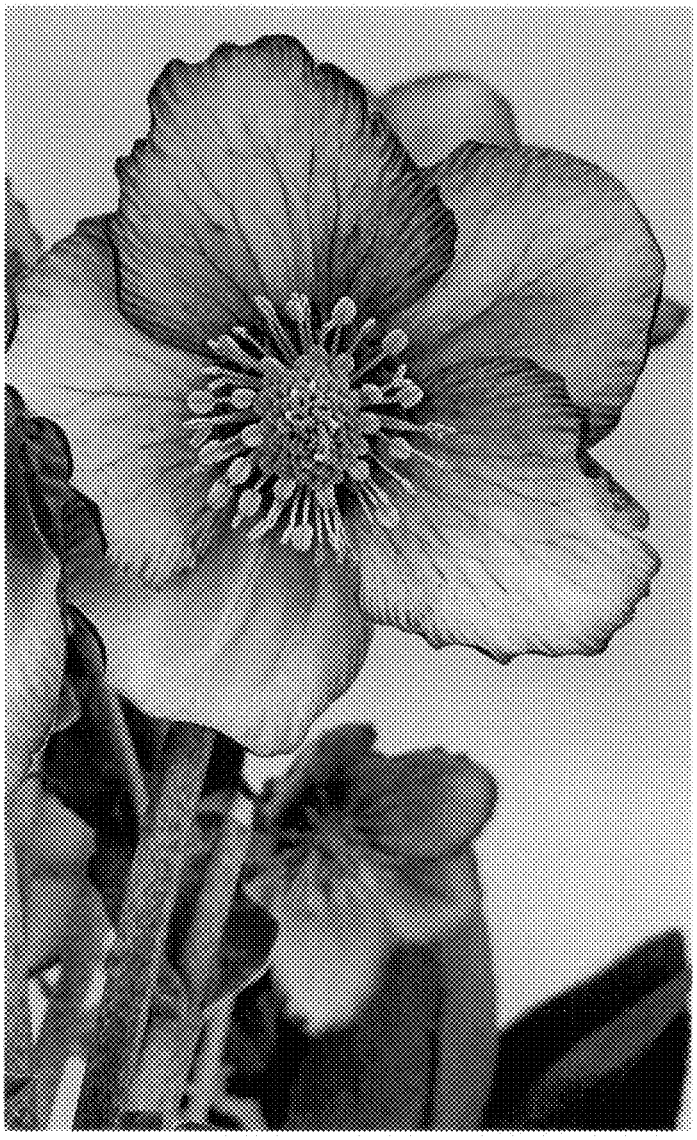

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant. The photograph on the first sheet (FIG. 1) is a side perspective view of a typical flowering plant of 'ET EPB 855' grown in a container. The photograph on the second sheet (FIG. 2) is a close-up view of a typical flowering plant of 'ET EPB 855'.

DETAILED BOTANICAL DESCRIPTION

The aforementioned photographs and following observations, measurements and values describe plants grown during the winter in two- liter containers in an outdoor nursery in Boijl, The Netherlands and under cultural practices typical of commercial *Helleborus* production. During the production of the plants, day temperatures ranged from 0° C. to 10° C. and night temperatures ranged from -15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus orientalis* X *Helleborus ericsmithii* 'ET EPB 855'.

Parentage:

*Female, or seed, parent*.—Proprietary selection of *Helleborus orientalis* identified as code number O15-315, not patented.

*Male, or pollen, parent*.—Proprietary selection of *Helleborus ericsmithii* identified as code number P14-1603, not patented.

Propagation:

*Type*.—By meristem culture.

*Time to initiate roots, summer*.—About 15 days at temperatures about 22° C. to 25° C.

*Time to initiate roots, winter*.—About 15 to 22 days at temperatures about 5° C. to 10° C.

*Time to produce a rooted young plant, summer*.—About two months at temperatures about 20° C.

*Time to produce a rooted young plant, winter*.—About 55 to 60 days at temperatures about 12° C.to 15° C.

*Root description*.—Fleshy, vigorous; typically white to brown in color, actual color of the roots is dependent on substrate composition, water quality, fertilizer type and formulation, substrate temperature and physiological age of roots.

*Rooting habit*.—Freely branching; moderately dense.

Plant description:

*Plant and growth habit*.—Herbaceous perennial; relatively compact and upright plant habit with flowers held above the foliar plane; moderately vigorous to vigorous growth habit and moderate growth rate.

*Plant height*.—About 45 cm to 50 cm.

*Plant diameter* (*area of spread*).—About 40 cm to 45 cm.

*Stems*.—Strength: Strong. Aspect: Mostly upright. Texture and luster: Smooth, glabrous; glossy. Color: Close to 146B densely covered with spots, close to 187B.

Leaf description:

*Arrangement*.—Leaves arranged alternately in a basal rosette; leaves palmately compound with about five to six leaflets per leaf.

*Leaflet length*.—About 5 cm to 15 cm.

*Leaflet width*.—About 3 cm to 7 cm.

*Leaflet shape*.—Elliptic to ovate.

*Leaflet apex*.—Acute.

*Leaflet base*.—Acute.

*Leaflet margin*.—Serrate.

*Leaflet texture and luster, upper surface*.—Smooth, glabrous; leathery; glossy.

*Leaflet texture and luster, lower surface*.—Smooth, glabrous; leathery; somewhat glossy.

*Leaflet venation pattern*.—Pinnate to palmate.

*Leaflet color*.—Developing leaves, upper surface: Close to 137A marbled with close to 139D. Developing leaves, lower surface: Close to 147B slightly tinged with close to 187A. Fully expanded leaves, upper surface: Close to 139A marbled with close to 139C to 139D; venation, close to 139C to 139D and proximally, close to 200B. Fully expanded leaves, lower surface: Close to 147B slightly tinged with close to 187A; venation, close to N186C.

*Petioles*.—Length, fully expanded leaves: About 20 cm. Diameter, fully expanded leaves: About 5 mm to 7 mm. Texture, upper and lower surfaces: Smooth, glabrous. Color, upper surface: Close to 146A; densely covered with spots, close to N186C; with development, spots, close to N199A. Color, lower surface: Close to 146A; densely covered with spots, close to N199A; with development, spots, close to 200B.

Flower description:

*Flower shape and habit*.—Single rotate flowers arranged in loosely branched cymes; freely flowering habit with typically about 35 flowers developing per cyme, and more flowers per cyme in the second year of growth; flowers facing outwardly to somewhat drooping.

*Fragrance*.—None detected.

*Natural flowering season*.—Plants begin flowering about two months after planting; plants flower from January through March in The Netherlands.

*Flower longevity on the plant*.—About two to three months; flowers persistent.

*Inflorescence height*.—About 25 cm.

*Inflorescence diameter*.—About 35 cm.

*Flower buds*.—Length: About 2 cm to 4 cm. Diameter: About 1 cm to 2.5 cm. Shape: Ovoid. Color: Close to 138D and 71A.

*Flower diameter*.—About 6 cm to 8 cm.

*Flower depth* (*height*).—About 2 cm to 4 cm.

*Petals*.—None observed; all transformed into nectaries.

*Sepals*.—Quantity and arrangement: Five, or occasionally six, arranged in a single whorl; slightly imbricate. Length: About 3 cm to 5 cm. Width: About 4 cm. Shape: Ovate to obovate. Apex: Obtuse and occasionally slightly emarginate. Base: Rounded. Margin: Mostly entire and occasionally slightly emarginate. Texture and luster, upper and lower surfaces: Smooth, glabrous; matte. Color: When opening and fully opened, upper surface: Center, close to 145A to 145B; towards the margins, close to 71A; venation, close to 145A to 145B or 71A; color does not change with subsequent development. When opening and fully opened, lower surface: Close to 145A to 145B and 71A; venation, close to 145A to 145B or 71A; color does not change with subsequent development.

*Peduncles*.—Length: About 30 cm. Diameter: About 5 mm to 8 mm. Strength: Strong. Aspect: Mostly upright. Texture: Smooth, glabrous. Color: Close to 146B heavily covered with spots, close to 59A.

*Pedicels*.—Length: About 3 cm to 12 cm. Diameter: About 3 mm to 4 mm. Aspect: About 30° to 40° from peduncle axis to slightly drooping. Strength: Strong. Texture: Smooth, glabrous. Color: Close to 146B heavily covered with spots, close to 59A.

*Reproductive organs*.—Stamens: Quantity per flower: About 60. Filament length: About 2 cm. Filament color: Close to 155A. Anther shape: Elliptic to ovate. Anther length: About 3 mm. Anther color: Close to 149D. Pollen amount: Scarce. Pollen color: Close to 149D. Pistils: Quantity per flower: About five to seven. Pistil length: About 3 cm. Stigma shape: Club-shaped. Stigma color: Close to 155C. Style length: About 2 cm to 3 cm. Style color: Close to 149D; proximally, close to 142A. Ovary color: Close to 142A.

*Nectaries*.—Quantity per flower: About 10 to 15. Length: About 5 mm to 8 mm. Width: About 3 mm to 5 mm. Shape: Funnelform. Color: Close to N144C.

*Seeds and fruits*.—To date, seed and fruit development have not been observed on plants of the new *Helleborus*.

Garden performance: Plants of the new *Helleborus* have been observed to have good garden performance and to tolerate rain, wind and temperatures ranging from about -10° C. to about 35° C.

Pathogen & pest resistance: To date, plants of the new *Helleborus* have not been observed to be resistant to pathogens and pests common to *Helleborus* plants.

It is claimed:

1. A new and distinct *Helleborus* plant named 'ET EPB 855' as illustrated and described.

* * * * *